(12) United States Patent
Pajunk-Schelling et al.

(10) Patent No.: US 11,191,564 B2
(45) Date of Patent: Dec. 7, 2021

(54) UNIPOLAR CANNULA

(71) Applicant: Pajunk GmbH Medizintechnologie, Geisingen (DE)

(72) Inventors: Simone Pajunk-Schelling, Geisingen (DE); Martin Hauger, Donaueschingen (DE)

(73) Assignee: Pajunk GmbH Medizintechnologie, Geisingen (DE)

( * ) Notice: Subject to any disclaimer, the term of this patent is extended or adjusted under 35 U.S.C. 154(b) by 99 days.

(21) Appl. No.: 16/307,095

(22) PCT Filed: May 26, 2017

(86) PCT No.: PCT/EP2017/062791
§ 371 (c)(1),
(2) Date: Dec. 4, 2018

(87) PCT Pub. No.: WO2017/211601
PCT Pub. Date: Dec. 14, 2017

(65) Prior Publication Data
US 2019/0350617 A1    Nov. 21, 2019

(30) Foreign Application Priority Data

Jun. 6, 2016   (DE) ................ 10 2016 110 379.9

(51) Int. Cl.
*A61B 17/34* (2006.01)
*A61M 19/00* (2006.01)
(Continued)

(52) U.S. Cl.
CPC ......... *A61B 17/3403* (2013.01); *A61M 19/00* (2013.01); *A61N 1/0502* (2013.01);
(Continued)

(58) Field of Classification Search
CPC ...... A61M 5/158; A61M 19/00; A61M 25/01; A61M 2005/1587; A61M 2025/0007;
(Continued)

(56) References Cited

U.S. PATENT DOCUMENTS 3,147,750 A * 9/1964 Fry .................... A61B 17/3403
600/378
3,828,780 A    8/1974 Morrison
(Continued)

FOREIGN PATENT DOCUMENTS

DE    8715740    2/1988
DE    19828794   2/2000
(Continued)

OTHER PUBLICATIONS

World Intellectual Property Organization, "International Search Report" and English translation thereof, Issued in International Application No. PCT/EP2017/062791 dated Jul. 27, 2017, document of 9 pages.
(Continued)

*Primary Examiner* — Kami A Bosworth
(74) *Attorney, Agent, or Firm* — Akerman LLP; Peter A. Chiabotti

(57) ABSTRACT

The application provides a unipolar cannula that can have a metal cannula tube, a body part made of an electrically insulating plastic, attached to the proximal end of the cannula tube, a connector disposed on the body part for the introduction of a liquid into the cannula tube, and a stimulation cable, an electroconductive wire of which electrically contacts the cannula tube in the region of the body part. The stimulation cable can be mounted laterally on the body part by a mounting part made of an electrically insulating plastic, where the mounting part has an electroconductive contact element which is connected conductively to the wire, and
(Continued)

where the contact element engages into a recess of the body part and contacts the cannula tube when the mounting part is mounted on the body part.

5 Claims, 16 Drawing Sheets

(51) Int. Cl.
    *A61N 1/05*     (2006.01)
    *A61B 17/00*     (2006.01)
    *A61N 1/36*     (2006.01)

(52) U.S. Cl.
    CPC ........... *A61B 2017/00477* (2013.01); *A61B 2017/00862* (2013.01); *A61B 2017/3413* (2013.01); *A61N 1/3605* (2013.01)

(58) Field of Classification Search
    CPC ... A61M 2205/13; A61N 1/05; A61N 1/0502; A61N 1/0551; A61N 1/36017; A61N 1/36021; A61N 1/3605–1/36062; A61B 17/3401; A61B 17/3403; A61B 2017/00477; A61B 2017/3413
    See application file for complete search history.

(56) References Cited

U.S. PATENT DOCUMENTS

| | | | |
|---|---|---|---|
| 3,858,586 A * | 1/1975 | Lessen | A61B 17/42 606/49 |
| 4,824,433 A | 4/1989 | Maerz et al. | |
| 5,507,732 A * | 4/1996 | McClure | A61M 25/00 604/533 |
| 5,605,539 A | 2/1997 | Buelna et al. | |
| 5,766,167 A | 6/1998 | Eggers et al. | |
| 5,853,393 A | 12/1998 | Bogert | |
| 6,337,998 B1 | 1/2002 | Behl et al. | |
| 6,456,874 B1 | 9/2002 | Hafer et al. | |
| 7,022,115 B1 | 4/2006 | Meier et al. | |
| 7,120,487 B2 | 10/2006 | Nelson | |
| 2002/0198557 A1 | 12/2002 | Freigang | |
| 2007/0250021 A1 | 10/2007 | Brimhall et al. | |
| 2008/0058757 A1 | 3/2008 | Pajunk et al. | |
| 2009/0012578 A1 * | 1/2009 | Carrez | H01R 13/025 607/46 |
| 2010/0191193 A1 | 7/2010 | Pajunk et al. | |
| 2019/0105459 A1 * | 4/2019 | Lajarín Barquero | A61N 1/0502 |

FOREIGN PATENT DOCUMENTS

| | | |
|---|---|---|
| DE | 20107778 | 11/2001 |
| DE | 102007029229 | 12/2008 |
| EP | 1002500 | 5/2000 |
| JP | 2002355291 | 12/2002 |
| RU | 105574 | 6/2011 |
| WO | 2010012023 | 2/2010 |

OTHER PUBLICATIONS

Japanese Patent Office Action, Japanese Patent Office, dated Feb. 9, 2021, with translation.

* cited by examiner

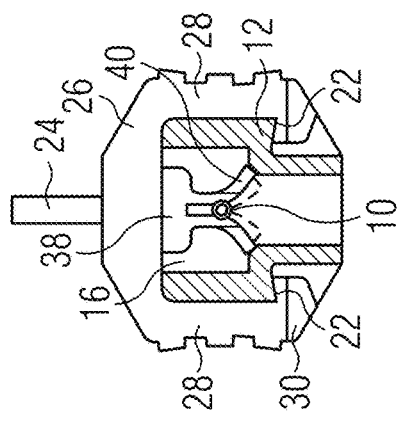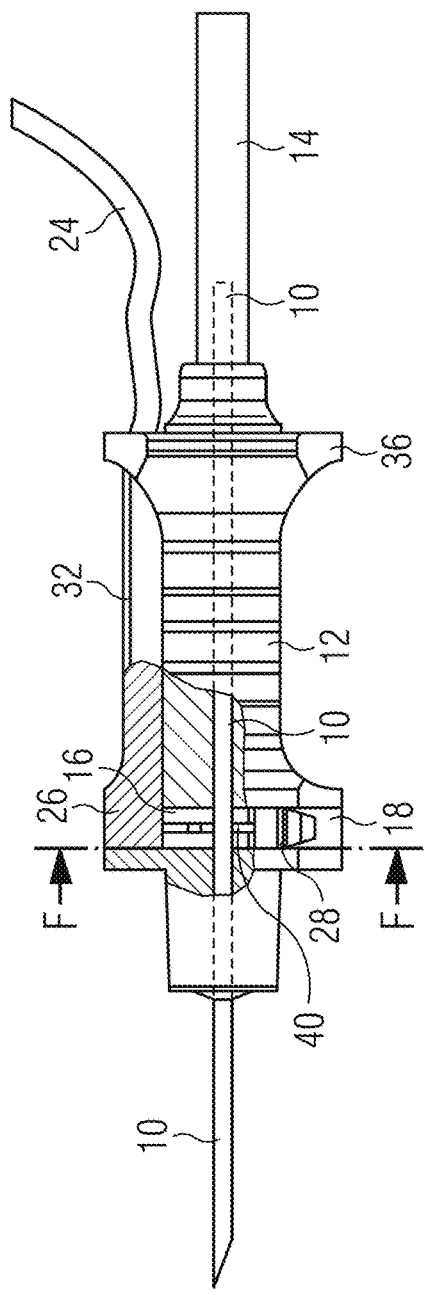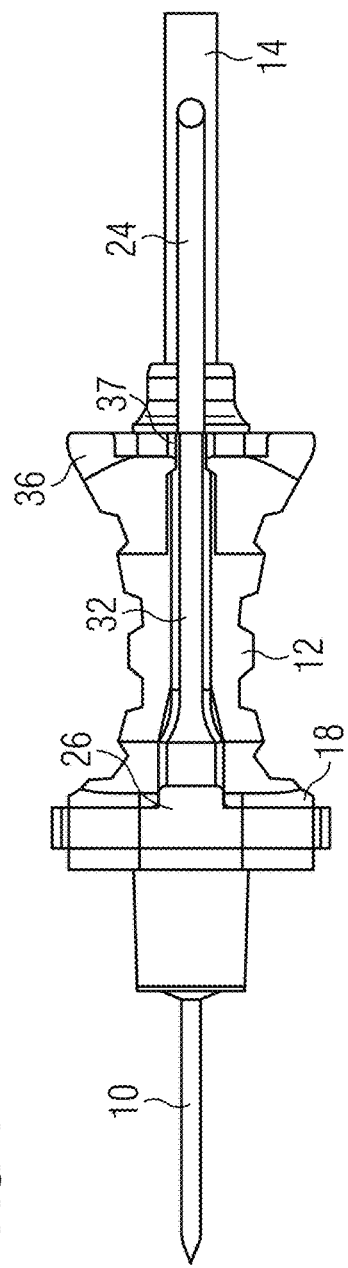

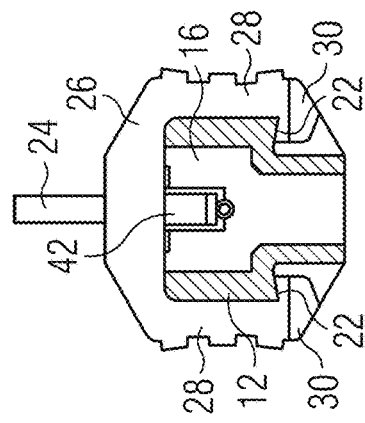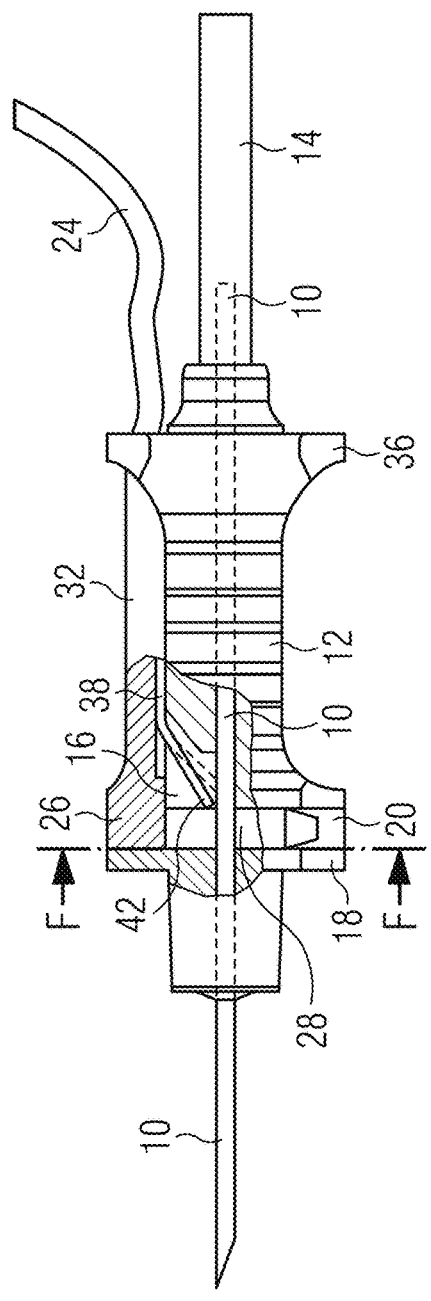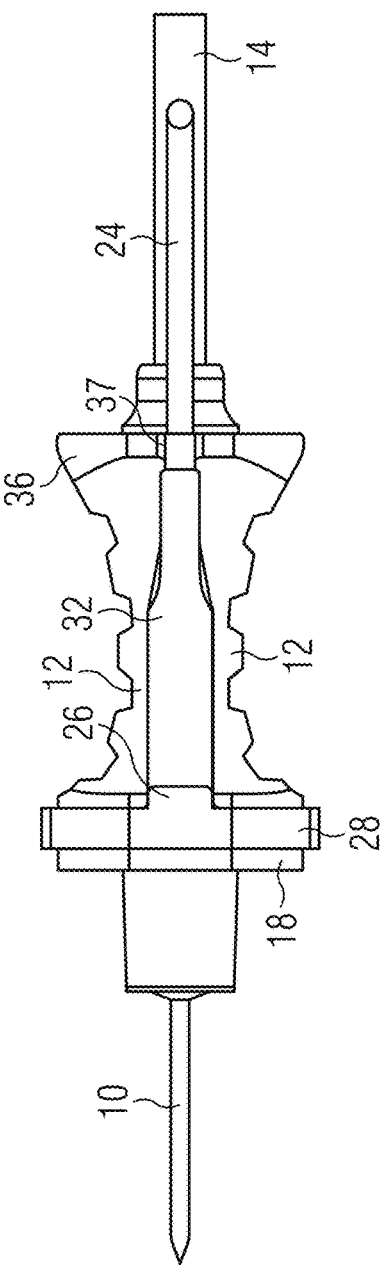

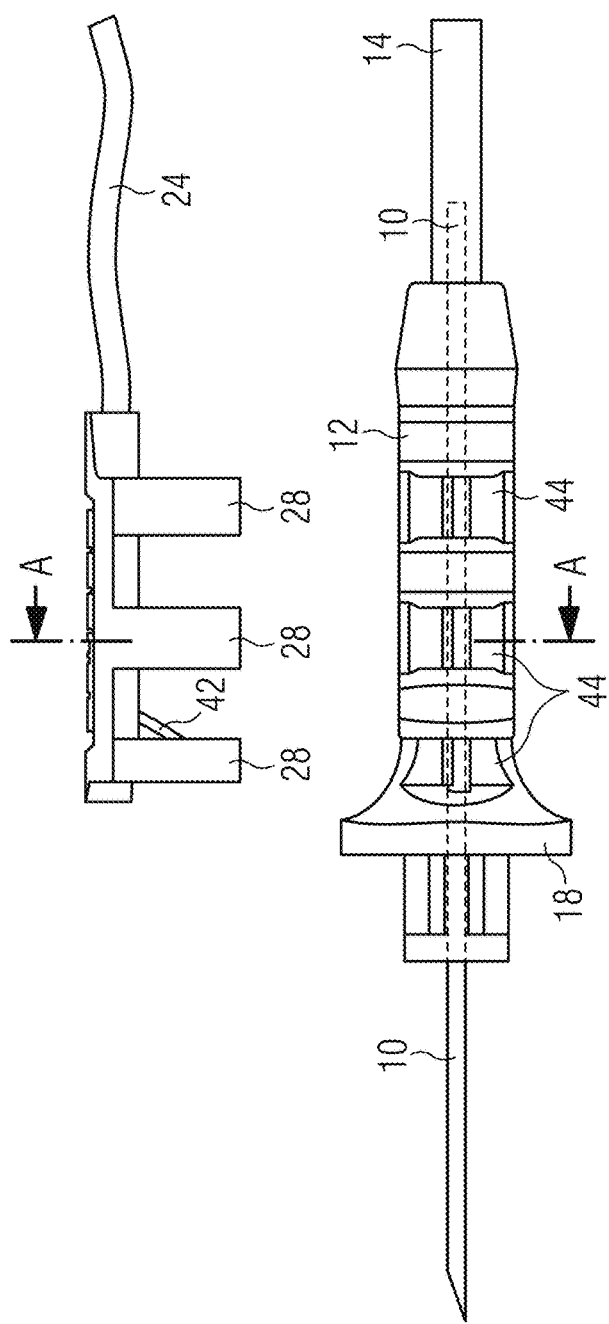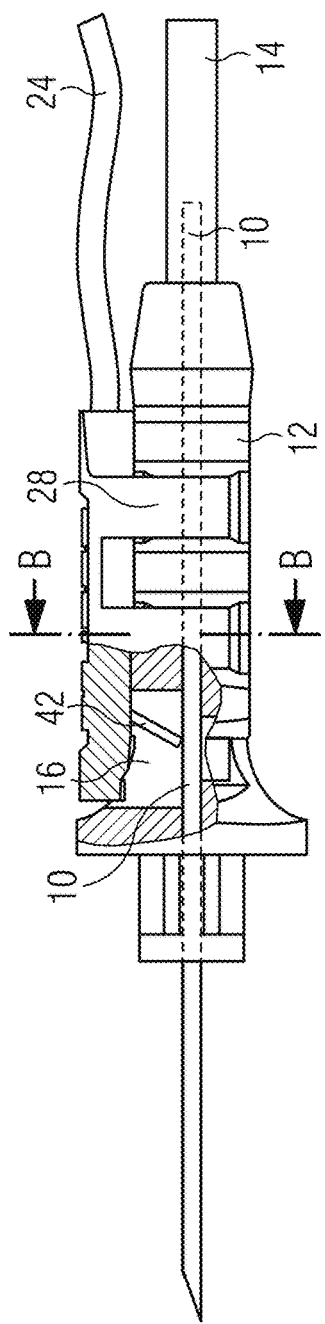

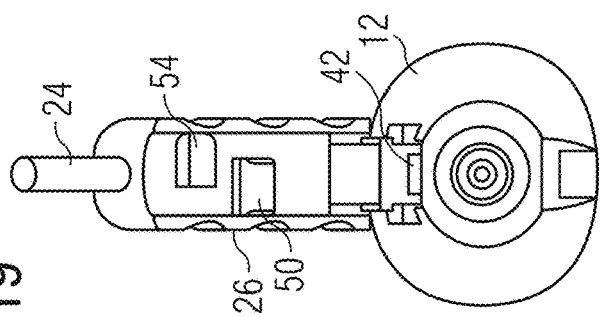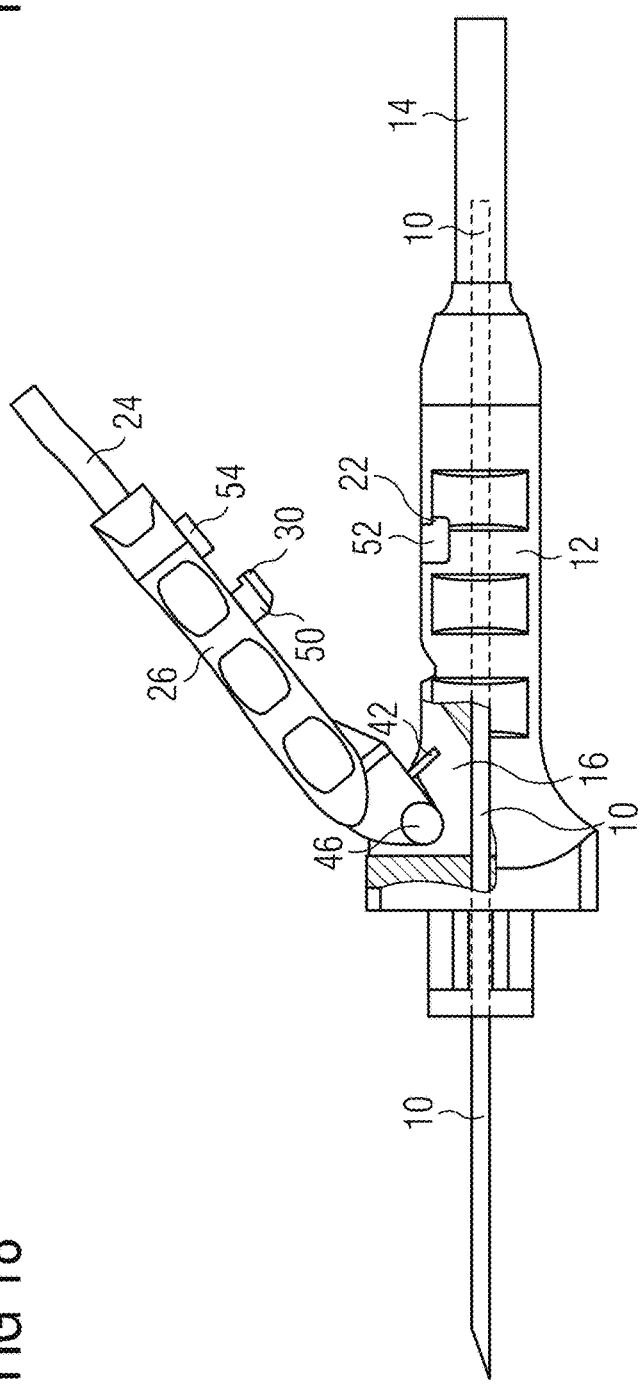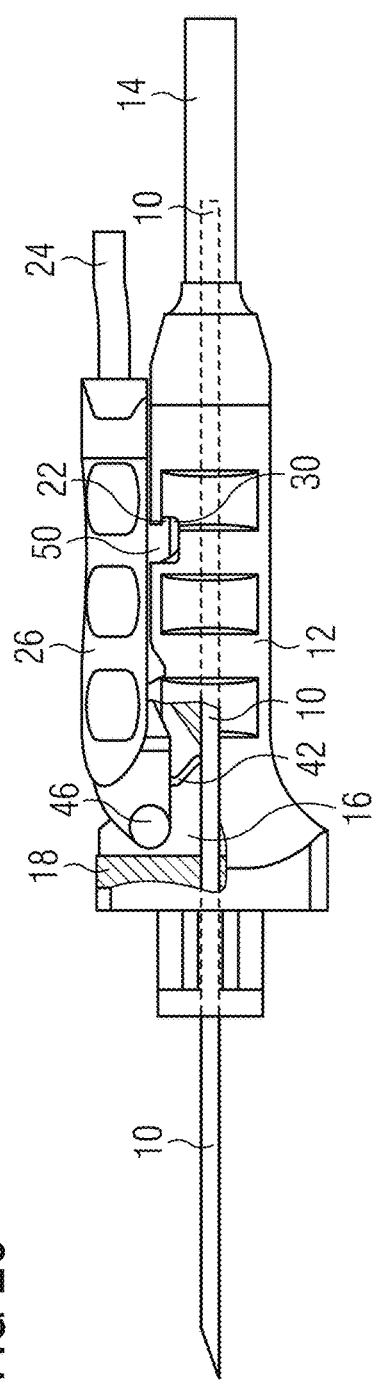

FIG 21
a)
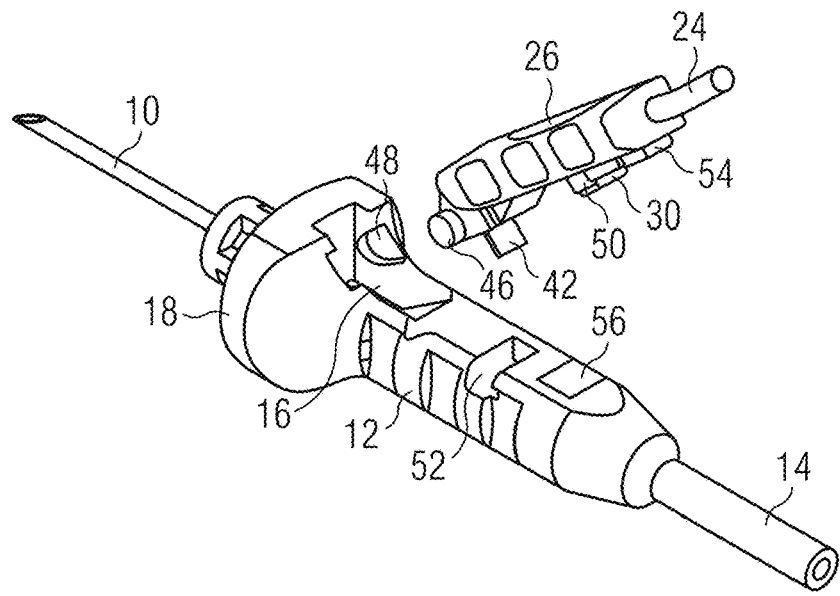
b)
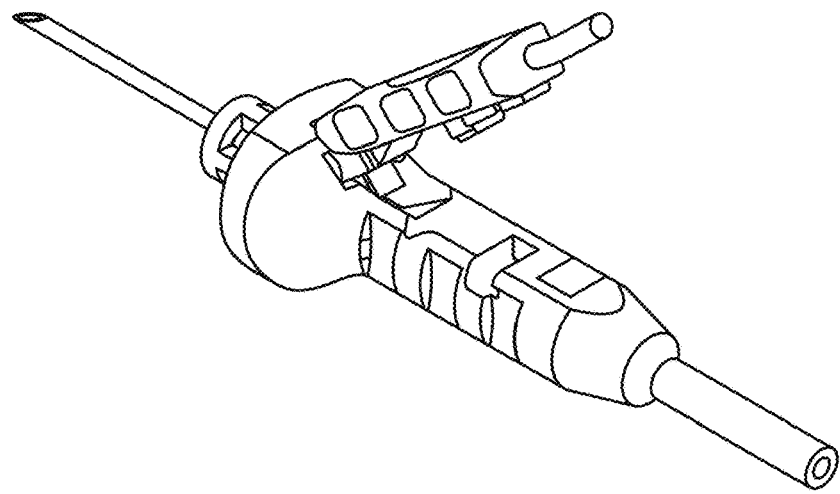
c)
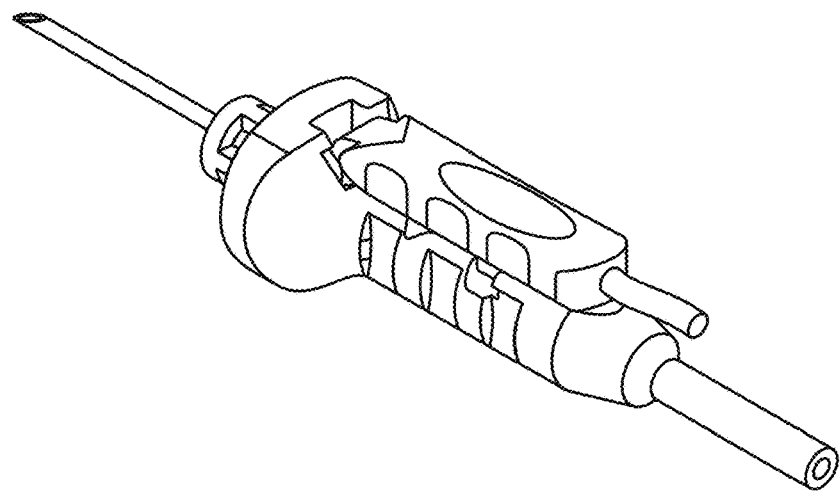

FIG 26
a)
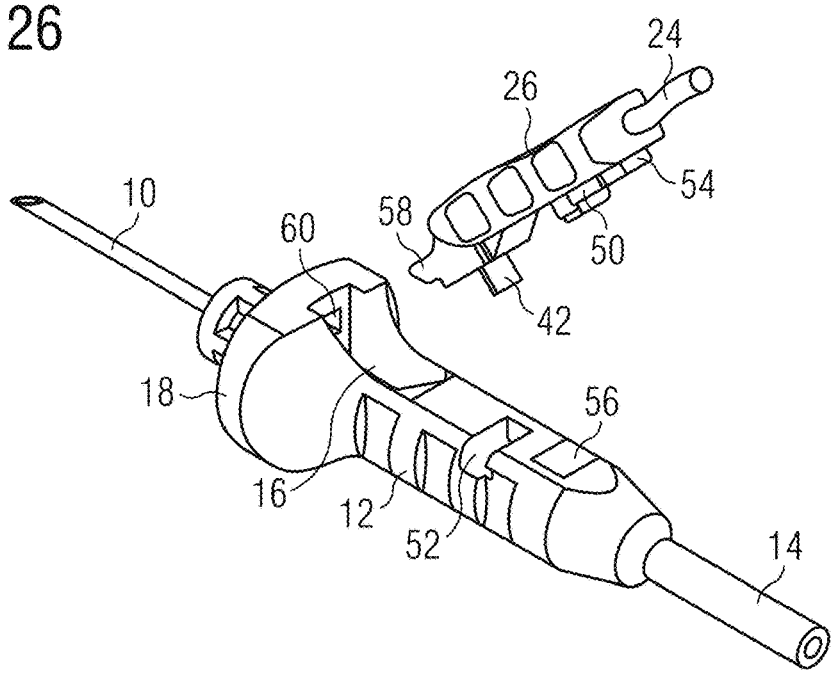
b)
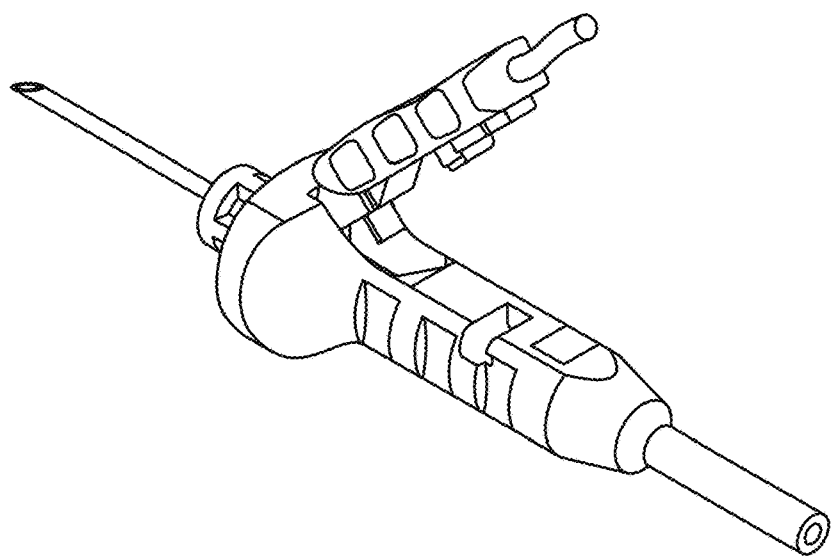
c)
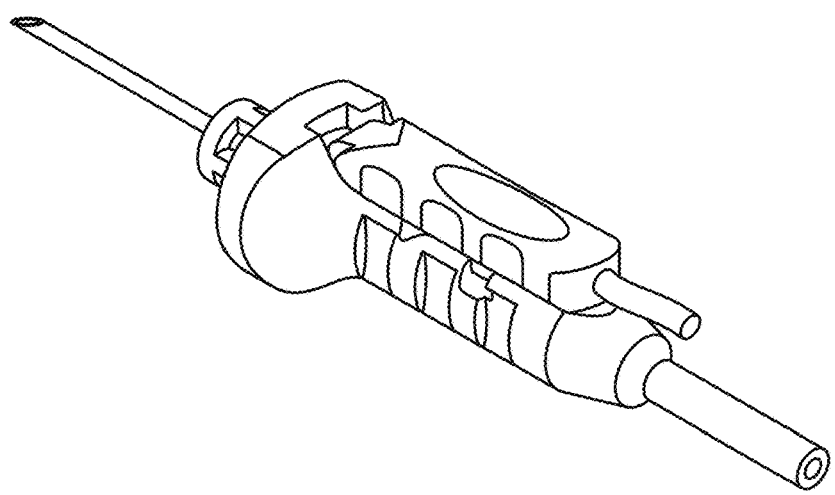

A-A

UNIPOLAR CANNULA

CROSS REFERENCE TO RELATED APPLICATIONS

This application is a § 371 National Phase of PCT/EP2017/062791, filed May 26, 2017, the entirety of which is incorporated by reference and which claims priority to German Patent Application No. 10 2016 110 379.9, filed Jun. 6, 2016.

BACKGROUND

The application relates to a unipolar cannula.

In such unipolar cannulas, the position of the distal cannula tip, e.g. on a nerve, is determined by electrical stimulation. The electrical stimulation pulses are supplied via a stimulation cable, which contacts the electrically conductive cannula tube in the region of a proximal body part of the cannula. Unipolar cannulas of this type are known, for example, from U.S. Pat. No. 7,022,115 B1 and from EP 1 002 500 A1 and are used in particular in anesthesia for the purpose of peripheral nerve blockage.

In these known unipolar cannulas, the stimulation cable is permanently connected to the cannula in that the insulating sheath of the stimulation cable is connected to the body part, which is made of plastic, and the electrically conductive wire of the stimulation cable is molded into the body part, contacting the metal cannula tube on the interior of the body part.

Recently, the use of ultrasound to monitor and verify the position of a cannula during anesthesia has become more common. For this purpose, an ultrasound probe placed on the body's surface emits ultrasonic signals and receives the ultrasonic signals that are reflected by the metal cannula. Due to the improved ultrasound visibility of the cannula, as described, for example, in WO 2010/012023 A1, anesthesiologists are increasingly limiting themselves to ultrasonic cannula detection and are dispensing with electrostimulation.

SUMMARY

The application provides a cannula that expediently combines both ultrasound and electrostimulation capabilities for detecting the position of a cannula.

Advantageous embodiments are disclosed herein.

The application is directed to an arrangement where, rather than being permanently connected to the cannula, the stimulation cable can be optionally attached to the body part of the cannula. If the unipolar cannula will be used only with ultrasound position detection, the stimulation cable will not be used, and therefore remains disconnected from the cannula, or a stimulation cable attached to the cannula is removed from the cannula. This prevents any interference by the stimulation cable and allows the cannula to be used as a conventional cannula without electrostimulation. If positioning by means of electrostimulation is desired, the same cannula can be used by simply attaching the stimulation cable laterally to the body part, or by leaving a stimulation cable that is already attached to the cannula in place on the cannula, where the conductive wire of the stimulation cable is forced into contact with the metal cannula tube. The same cannula can thereby be used either with or without electrostimulation.

To mount the stimulation cable on the body part of the cannula, a mounting part made of an electrically insulating plastic is used, which can be mounted laterally on the body part such that it rests against the outer periphery thereof. The mounting part includes an electroconductive contact element, which is electroconductively connected to the wire of the stimulation cable. The contact element and the wire may be permanently connected, e.g. by a solder joint, or may be connected to one another by a plug-in connection. When the mounting part is attached to the body part, the contact element engages into a recess in the body part, leaving the metal cannula tube exposed so that the contact element can conductively contact the cannula tube. In this position, the mounting part completely covers the outside of the contact element, thereby insulating the contact element and the connection thereof to the wire of the stimulation cable along the outer periphery of the body part, preventing contact by the user. In this way, the structural measures required for mounting the stimulation cable and for contacting the cannula tube do not affect the outer configuration of the body part, and as a result, the handling of the cannula without the stimulation cable is unimpeded and corresponds completely to a conventional cannula without electrical stimulation.

In one preferred embodiment, the stimulation cable can be mounted by means of a mounting part, which is attached to the body part via a snap connection. The snap connection can be effected, for example, by resilient snap-locking arms of the mounting part, which engage on the body part. In one embodiment, the contact element is preferably disposed between one or more pairs of snap-locking arms. In that case, the snap-locking arms are attached diametrically opposite one another on the two sides of the body part, with the recess for engagement of the contact element being situated in the region of the body part between the snap-locking arms. In another embodiment, the mounting part is mounted pivotably on the body part and locks onto the body part when pivoted against it.

The contact element for electrically contacting the cannula tube may be configured in a number of ways; it is necessary to ensure only that the contact element establishes good, reliable electrical contact with the cannula tube when the mounting part is attached to the body part. In one embodiment, the contact element may be embodied as an insulation displacement contact, which is pressed radially in the manner of a fork onto the cannula tube. The two arms of the insulation displacement contact are thereby pressed into the circumferential surface of the cannula tube to establish the necessary contact pressure.

In another embodiment, the contact element may be embodied as a spring tab, which rests on the outside of the cannula tube under elastic spring pressure when the mounting part is attached.

The proximal body part of the unipolar cannula is equipped with a port through which a liquid, in particular an anesthetic, can be introduced into the cannula tube to administer this liquid via the distal outlet opening of the cannula. The port is preferably coaxial to the cannula tube, which is made possible by the lateral attachment of the stimulation cable. The port can be configured, for example, as a connector, in particular as a luer lock connector. This connector may be formed directly on the body part, as shown, e.g. in U.S. Pat. No. 7,022,115 B1. Alternatively, the connector may be attached to a tube which is attached coaxially to the body part, as shown, e.g. in EP 1 002 500 A1.

BRIEF DESCRIPTION OF THE DRAWINGS

In the following, the disclosure will be elucidated in greater detail in reference to exemplary embodiments illustrated in the set of drawings. In the drawings:

FIG. 3 shows a partially axially cutaway side view of the unipolar cannula with the stimulation cable attached, FIG. 4 shows a plan view of the unipolar cannula, FIG. 5 shows a cross-section of the unipolar cannula with attached stimulation cable along section line F-F in FIG. 3, FIG. 9 shows an axially partially cut-away side view of the unipolar cannula with stimulation cable attached, FIG. 10 shows a plan view of the unipolar cannula of the second embodiment with stimulation cable attached, FIG. 11 shows a cross-section along section line F-F in FIG. 9 of the unipolar cannula with stimulation cable attached, FIG. 14 shows a side view of the unipolar cannula of the third embodiment with the stimulation cable removed, FIG. 15 shows a cross-section along the section line A-A in FIG. 14, FIG. 16 shows a partially axially cut-away side view of the unipolar cannula of the third embodiment with stimulation cable attached, FIG. 17 shows a cross section along section line BB in FIG. 16, FIG. 18 shows a partially axially cut-away side view of a fourth embodiment of the unipolar cannula, FIG. 19 shows an axial view from the proximal end of the unipolar cannula of FIG. 18, FIG. 20 shows a partially axially cut-away side view of the unipolar cannula of the fourth embodiment, corresponding to FIG. 18, with stimulation cable attached, FIGS. 21a, b and c show the mounting of the stimulation cable on the unipolar cannula of the fourth embodiment in three steps.

DETAILED DESCRIPTION

Figure 1:
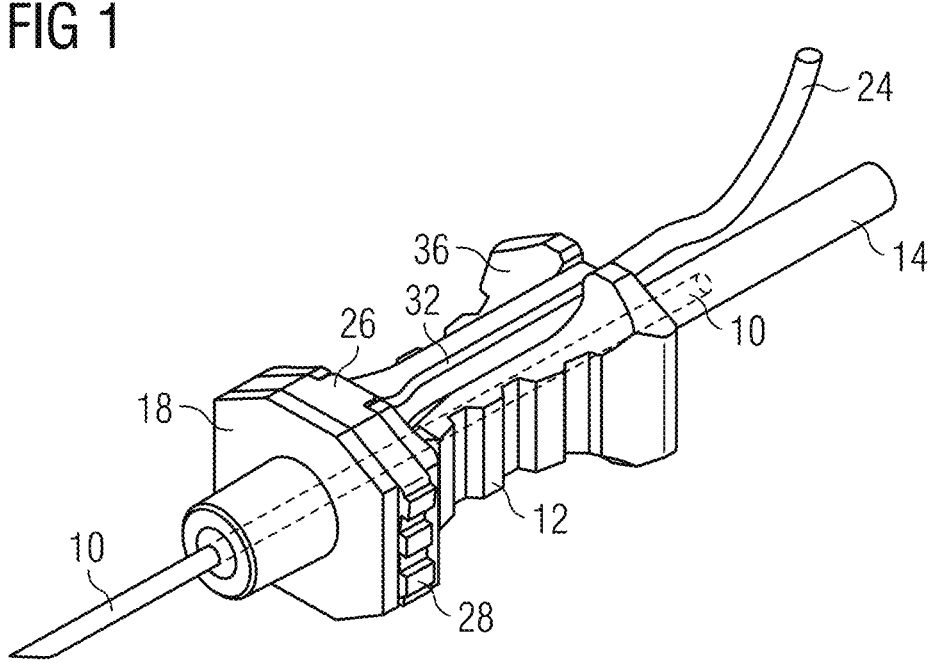
FIG. 1 shows a perspective view of a first embodiment of the unipolar cannula, with the stimulation cable attached.
Figure 2:
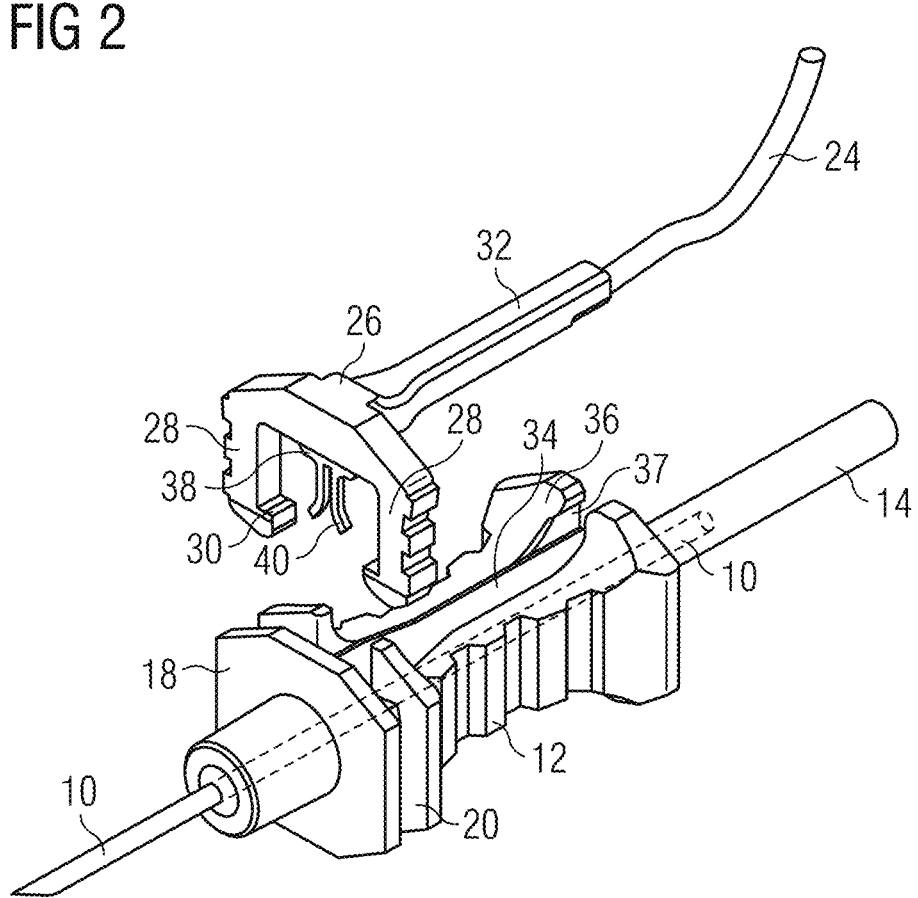
FIG. 2 shows a corresponding perspective view of the unipolar cannula with the stimulation cable removed.
Figure 6:
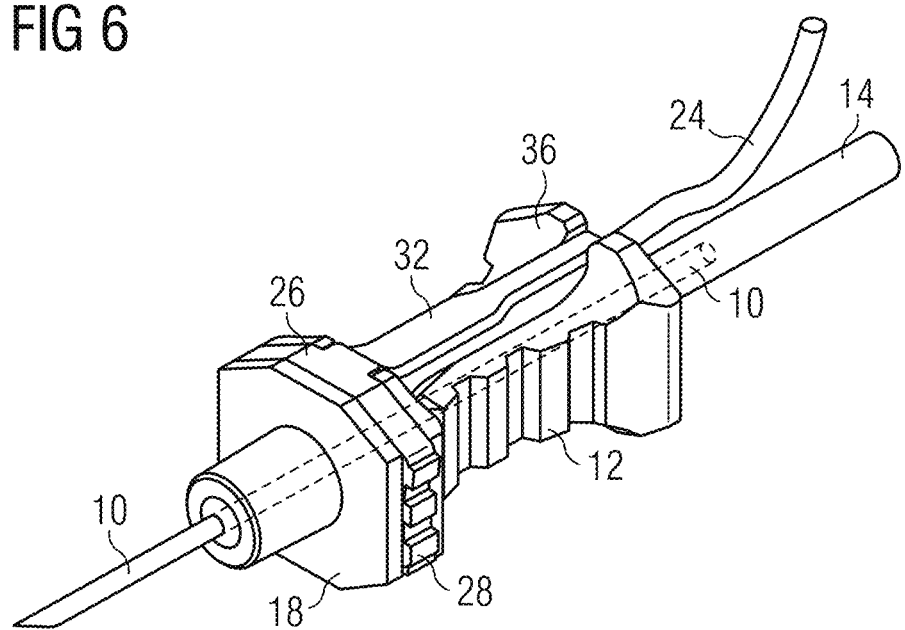
FIG. 6 shows a perspective view of a second embodiment of the unipolar cannula with stimulation cable attached.
Figure 7:
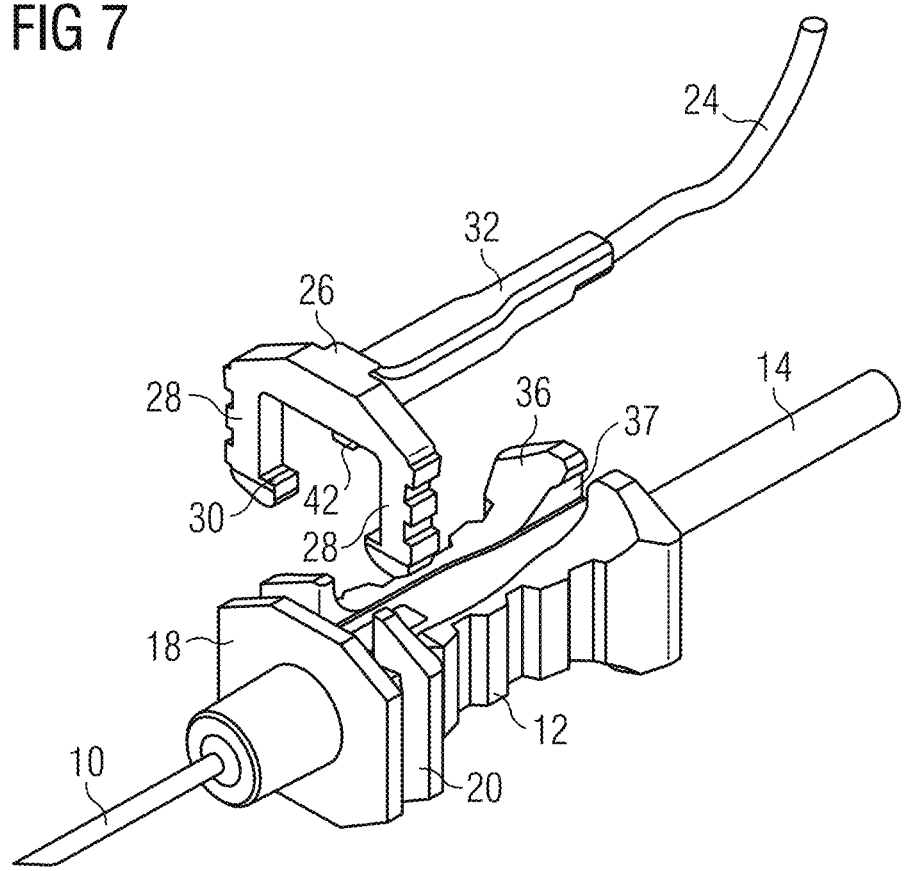
FIG. 7 shows a corresponding perspective view of the second embodiment of the unipolar cannula with the stimulation cable removed.
Figure 8:
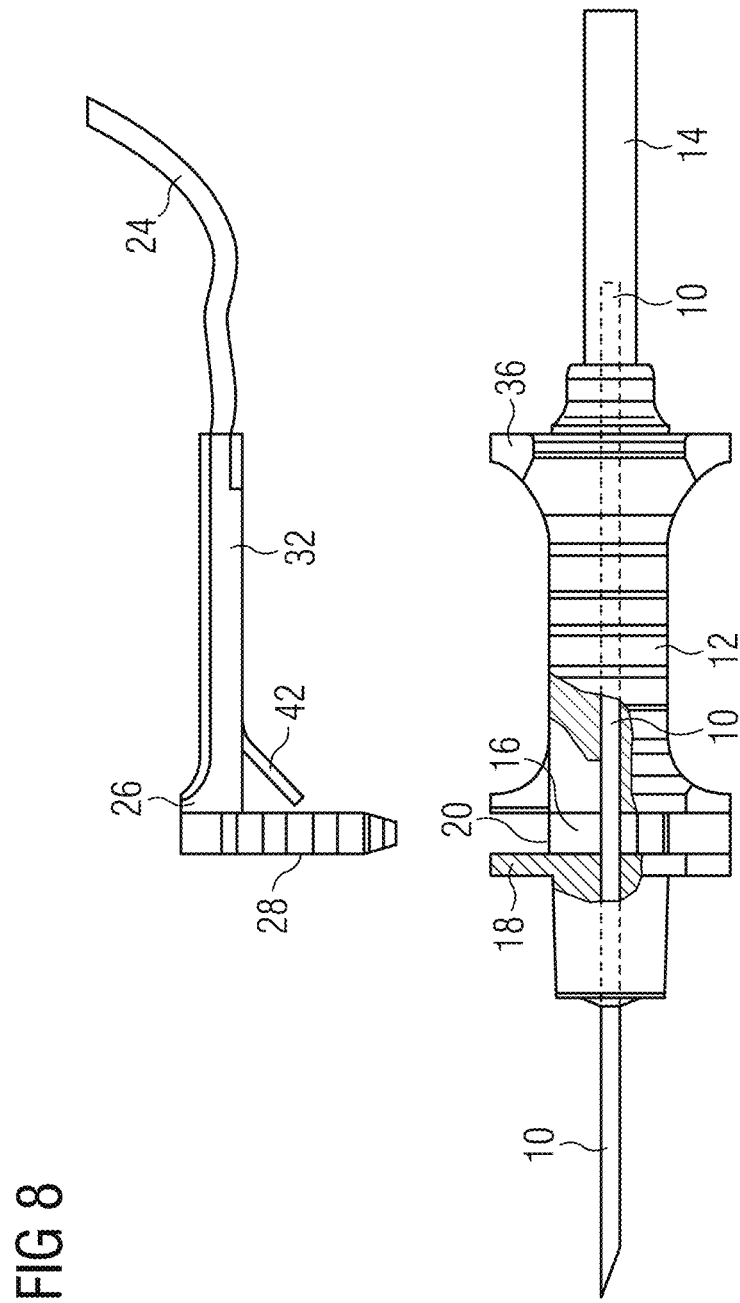
FIG. 8 shows a partially axially cut-away side view of the unipolar cannula of the second embodiment with the stimulation cable removed.
Figure 12:
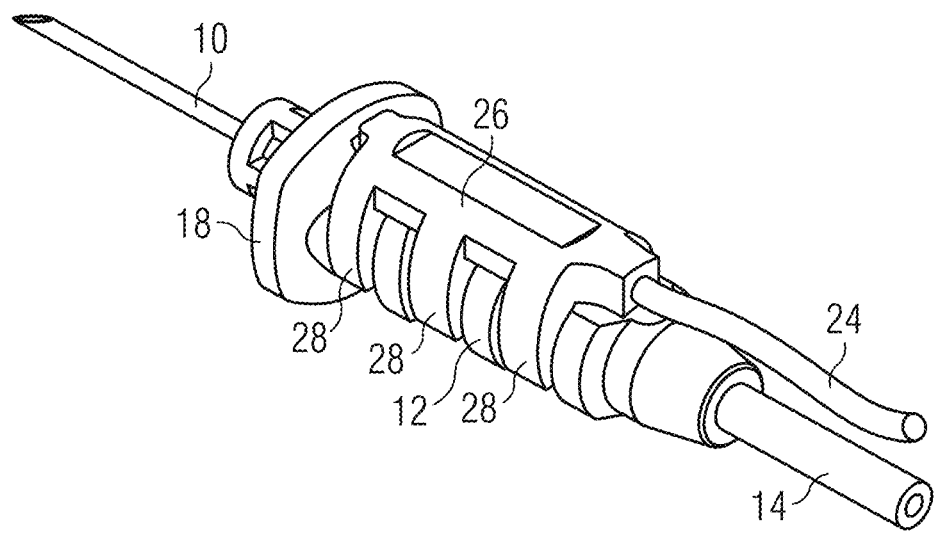
FIG. 12 shows a perspective view of a third embodiment of the unipolar cannula with stimulation cable attached.
Figure 13:
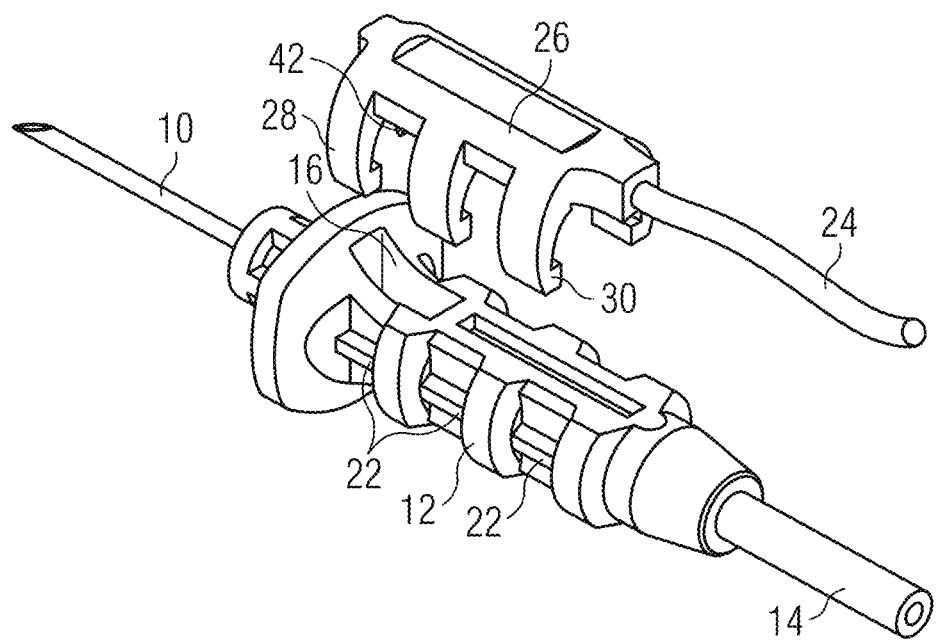
FIG. 13 shows a perspective view of this third embodiment with the stimulation cable removed.

FIGS. 1 to 5 illustrate a first exemplary embodiment of the unipolar cannula.

The unipolar cannula has a metal cannula tube 10, the outer circumferential surface of which is coated with an electrically insulating plastic, leaving only the distal tip of the metal cannula tube 10 exposed. At the proximal end, cannula tube 10 is molded onto a body part 12 made of plastic. Body part 12 is essentially in a conventional rectangular parallelepiped shape, the forward and rear ends of which are widened to a flange to allow the cannula to be securely gripped and guided using two fingers. Cannula tube 10 extends axially through body part 12. The end of cannula tube 10 that protrudes proximally from body part 12 is enclosed within a coaxial tube 14, which is attached sealed to body part 12. Tube 14 serves as an injection tube, through which a liquid, e.g. an anesthetic, can be introduced into the cannula tube 10 and then exits the cannula tube 10 distally. At its unattached end, not shown in the drawing, tube 14 has a connector, e.g. a luer lock connector, to which a syringe or the like for supplying the liquid can be attached. Alternatively, if no injection tube is desired the connector may be located directly on body part 12.

In its distal section, body part 12 is provided with a recess 16, which is open toward the upper lateral surface of body part 12 in the drawing, and the depth of which extends at least down to cannula tube 10. In the exemplary embodiment shown, recess 16 is open diametrically continuously through body part 12. In its axial section that extends within recess 16, cannula tube 10 is exposed, i.e. in this section, metal cannula tube 10 has no insulating outer coating. In the forward distal widened flange 18 of body part 12, a groove 20 is formed, extending circumferentially. Groove 20 is formed diametrically on both sides of recess 16, with recess 16 extending distally into groove 20. On the bottom side in the drawings, groove 20 has an inner step 22 on each of the two sides.

When the unipolar cannula will be used for electrostimulation, a stimulation cable 24, which can be connected to an electrical stimulation device, is mounted on body part 12. Stimulation cable 24 has a mounting part 26, which is made of an electrically insulating plastic and is attached to the insulation of the stimulation cable. Mounting part 26 can be mounted on body part 12 by means of a snap connection. In the exemplary embodiment shown, the snap connection is formed by a pair of resilient snap-snap-locking arms 28 of mounting part 26. Snap-locking arms 28 are configured as U-shaped limbs, which are shaped such that they can be inserted into groove 20 and thereby engage diametrically around body part 12 in the region of groove 20 on both sides of recess 16. At the unattached end of each snap-locking arm 28, an inwardly directed nib 30 is formed. To place mounting part 26 with snap-locking arms 28 onto body part 12 laterally in the radial direction, snap-locking arms 28 are inserted into groove 20, with the nib 30 of each arm snapping in behind the respective inner step 22.

Mounting part 26 is thereby clipped onto body part 12 and secured on body part 12. In said position, mounting part 26 fits with snap-locking arms 28 into the outer contour of forward flange 18. When mounting part 26 is in its clipped-on position, a proximally extending longitudinal member 32 of mounting part 26 fits into a groove 34, which extends axially in the upper lateral surface of the body part 12 in the drawing. Further along groove 34, the proximal rear flange 36 of body part 12 includes a notch 37 into which longitudinal member 32 engages. In its snapped-in state, mounting part 26 is thereby secured to body part 12 over the entire axial length of said body part 12.

The electroconductive wire of stimulation cable 24 is electroconductively connected to a metal contact element 38 located within mounting part 26. In the first exemplary embodiment, contact element 38 is embodied as an insulation displacement contact 40. Insulation displacement contact 40 is located centrally between the snap-locking arms 28 in the plane spanned by the snap-locking arms 28 and extends substantially parallel to the snap-locking arms 28. When mounting part 26 with snap-locking arms 28 is snapped onto body part 12, insulation displacement contact 40 protrudes radially into recess 16 and its two fork-shaped arms are pressed onto the exposed cannula tube 10. In that position, the arms of insulation displacement contact 40 are pressed into the surface of the metal cannula tube 10, as is clear in FIG. 5, in particular. As a result, when mounting part 26 is snapped on, a reliable electrical contact is established from the wire of the stimulation cable 24 via the insulation displacement contact 40 to the cannula tube 10. Mounting part 26 thereby covers contact element 38 on the outer circumferential surface of body part 12, insulating it completely.

A second exemplary embodiment is shown in FIGS. 6 to 11. To the extent that this exemplary embodiment is identical to the first embodiment, the same reference signs are used, and the foregoing description applies to this second exemplary embodiment as well.

The second exemplary embodiment differs from the first exemplary embodiment in terms of the configuration of contact element 38. In this second embodiment, contact element 38 is equipped with a spring tab 42, which is made of a conductive resilient metal and is conductively connected to the wire of stimulation cable 24. Spring tab 42 is set in the plastic of mounting part 26 in such a way that the spring tab is angled distally inward from longitudinal member 32 of mounting part 26, as is clear, in particular, in FIG. 8. When mounting part 26 is snapped onto body part 12 by means of snap-locking arms 28, spring tab 42 engages into recess 16 and comes to rest under elastic spring tension against the outer circumferential surface of the exposed cannula tube 10, as is clear from FIGS. 9 and 11. Spring tab 42 thereby establishes a reliable electrical contact between both the contact element 38 and the wire of stimulation cable 24, which is connected to contact element 38, and the cannula tube 10.

FIGS. 12 to 17 show a third embodiment of the unipolar cannula. To the extent that this exemplary embodiment is identical to the above-described first and second embodiments, the same reference signs are used, and the foregoing description applies to this third exemplary embodiment as well.

The third embodiment differs from the first and second embodiments in terms of the configuration of the snap connection between body part 12 and mounting part 26. In this third embodiment, mounting part 26 is equipped with three pairs of snap-locking arms 28, spaced apart from one another in the axial direction. The pairs of snap-locking arms 28 each engage around body part 12 and are fitted into correspondingly axially spaced grooves 44 in the periphery of body part 12, thereby attaching the stimulation cable. Inwardly directed nibs 30 on the respective snap-locking arms 28 engage behind inner steps 22 positioned within these grooves 44. Thus, when mounting part 26 is placed on body part 12, mounting part 26 engages in this manner with the three pairs of snap-locking arms 28 behind the inner steps 22, thereby securing mounting part 26 along with stimulation cable 24 on body part 12 over the entire axial length of said body part 12. In this position, the distally foremost pair of snap-locking arms 28 encompasses body part 12 in the region of recess 16. Contact element 38, which is located between the distally foremost snap-locking arms 28, is thereby placed in electroconductive contact with cannula tube 10 in recess 16, as is clear from FIG. 16. Contact element 38 may be embodied as a spring tab 42, as shown, in particular, in FIGS. 15 and 16. Of course, in this third embodiment, contact element 38 may also be embodied as an insulation displacement contact 40, as described in the first embodiment.

FIGS. 18 to 21 show a fourth embodiment of the unipolar cannula. To the extent that this fourth embodiment is identical to the above-described embodiments, the same reference signs are used, and the foregoing description applies to this third embodiment as well.

The fourth embodiment differs from the previous embodiments in terms of the way in which mounting part 26 is mounted on body part 12.

In this fourth embodiment, the distal end of mounting part 26 engages into recess 16. At the distal end of mounting part 26, bearing pins 46 are molded laterally, i.e. protruding perpendicular to the axial direction of the cannula. Upon insertion of mounting part 26 into recess 16, as shown in FIGS. 21a and 21b, these circular cylindrical bearing pins 46 are received by a bearing socket 48 formed in the proximally-facing wall of forward flange 18. When mounting part 26 is seated with its bearing pins 46 in bearing socket 48, mounting part 26 is disposed on body part 12 so as to pivot about the axis of bearing pin 46 that extends transversely to the cannula axis, as shown in FIGS. 18 and 21b.

Mounting part 26 can then be pivoted relative to body part 12 from the position shown in FIG. 18 into the position shown in FIG. 20, as is also shown in FIGS. 21b and 21c. As soon as mounting part 26 comes to rest against body part 12 (FIG. 20), a snap-locking arm 50, which is molded onto the surface of mounting part 26 that faces body part 12, engages into a depression 52 in the outer surface of body part 12. In this position, a nib 30 located at the unattached end of said snap-locking arm 50 engages behind an inner step 22 of depression 52, as is clear, in particular, in FIG. 20. Mounting part 26 is thereby secured over its entire axial length on body part 12.

Additionally, a protrusion 54 is molded onto the surface of mounting part 26 that faces body part 12. When mounting part 26 is pivoted toward body part 12 into the mounted position shown in FIG. 20, said protrusion 54 dips into a corresponding depression 56 in the outer surface of body part 12, thereby additionally securing mounting part 26 in a positive-locking connection against any transverse displacement relative to body part 12.

In the illustration of FIGS. 18 to 21, contact element 38 is embodied as a spring tab 42. Of course, contact element 38 may also be embodied as insulation displacement contact 40.

FIGS. 23 to 26 show a fifth embodiment of the unipolar cannula. To the extent that this embodiment is identical to the above-described embodiments, the same reference signs are used, and the foregoing description applies to this embodiment as well.

The fifth embodiment is substantially identical to the fourth embodiment shown in FIGS. 18 to 21 and differs from said fourth embodiment only in terms of the configuration of the pivotable bearing of mounting part 26 on body part 12.

Figure 22:
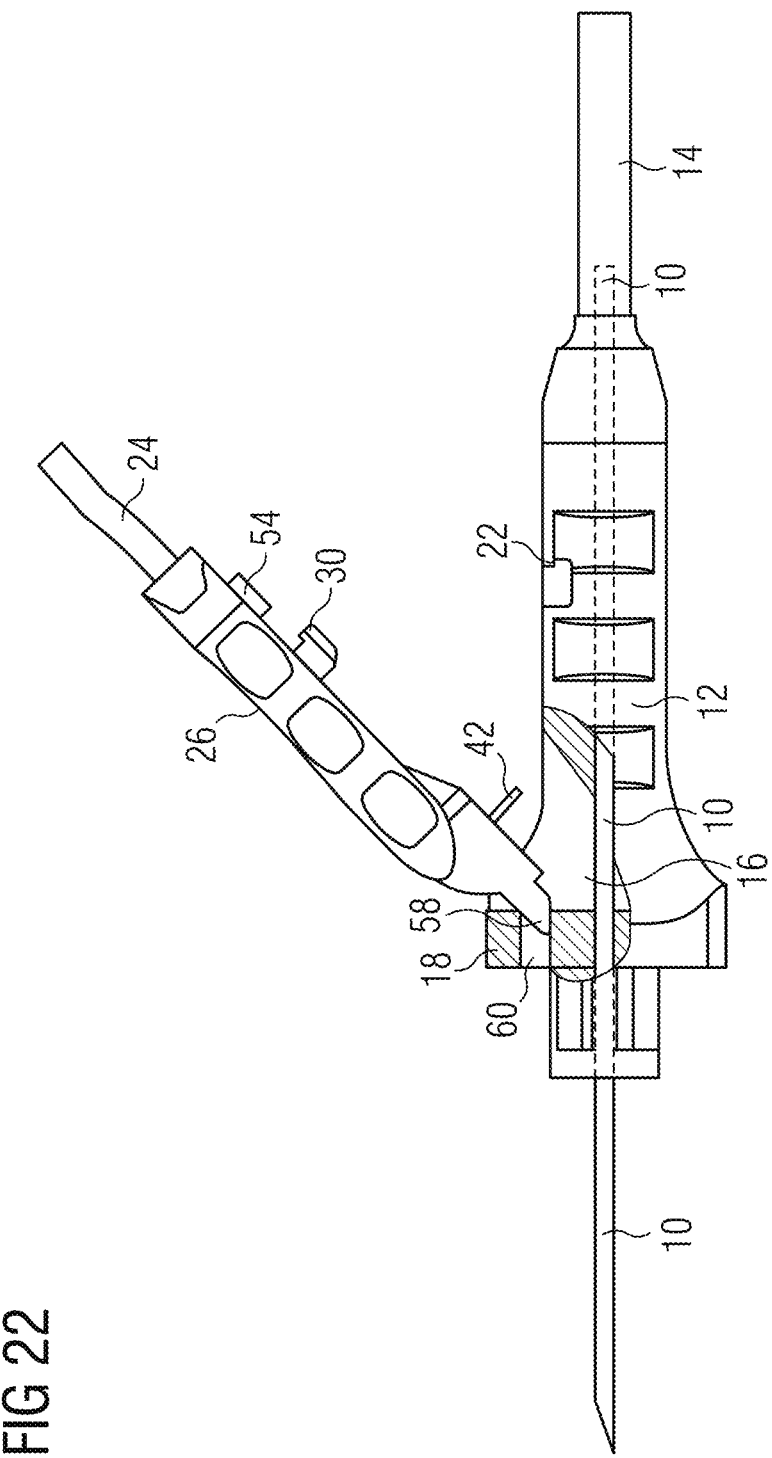
FIG. 22 shows a partially axially cut-away side view of a fifth embodiment of the unipolar cannula, with the stimulation cable removed.
Figure 23:
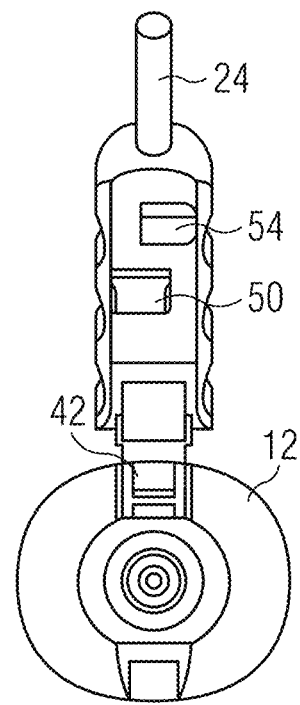
FIG. 23 shows an axial view from the proximal end of the unipolar cannula in the position shown in FIG. 22.
Figure 24:
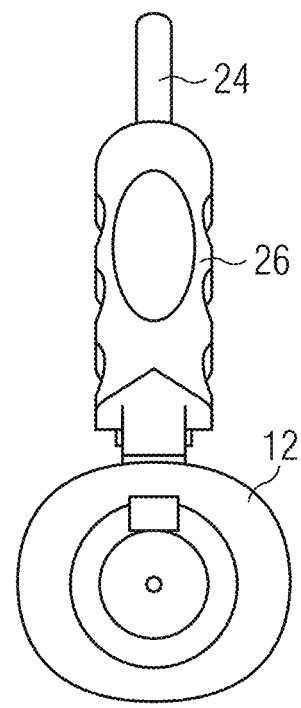
FIG. 24 shows a corresponding axial view from the distal end.
Figure 25:
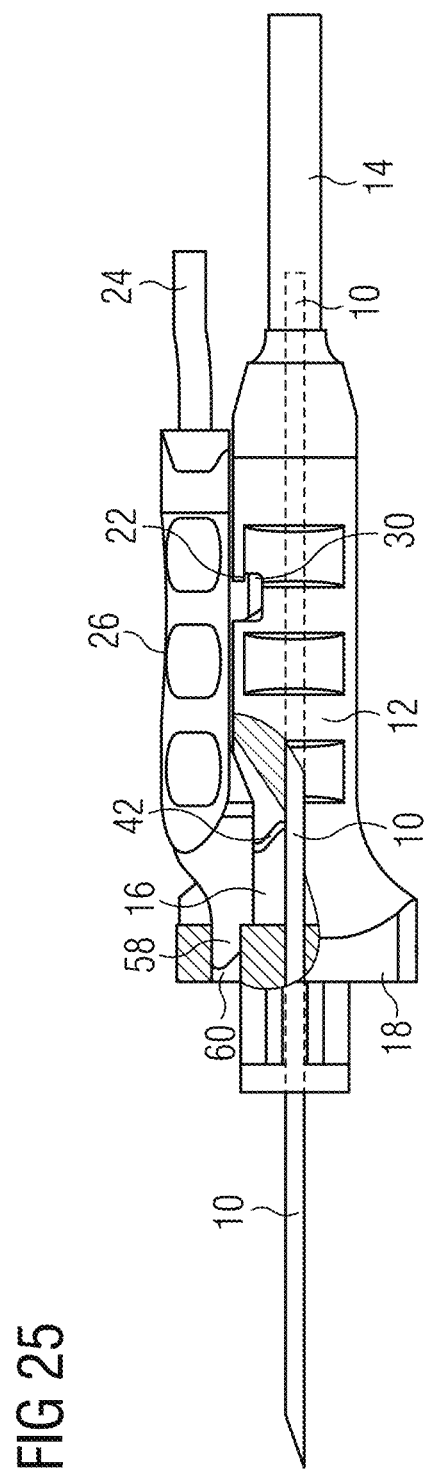
FIG. 25 shows a partially axially cut-away side view of the unipolar cannula of the fifth embodiment, with stimulation cable attached, FIGS. 26a, b and c show the mounting of the stimulation cable on the unipolar cannula of the fifth embodiment in three steps.
Figure 29:
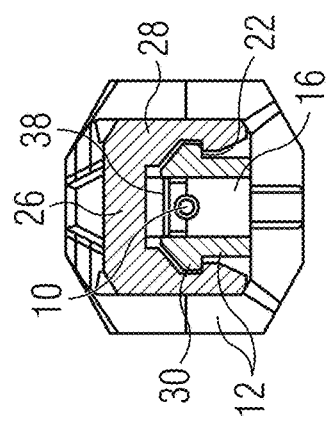
FIG. 29 shows a cross-section along line A-A in FIG. 27.
Figure 27:
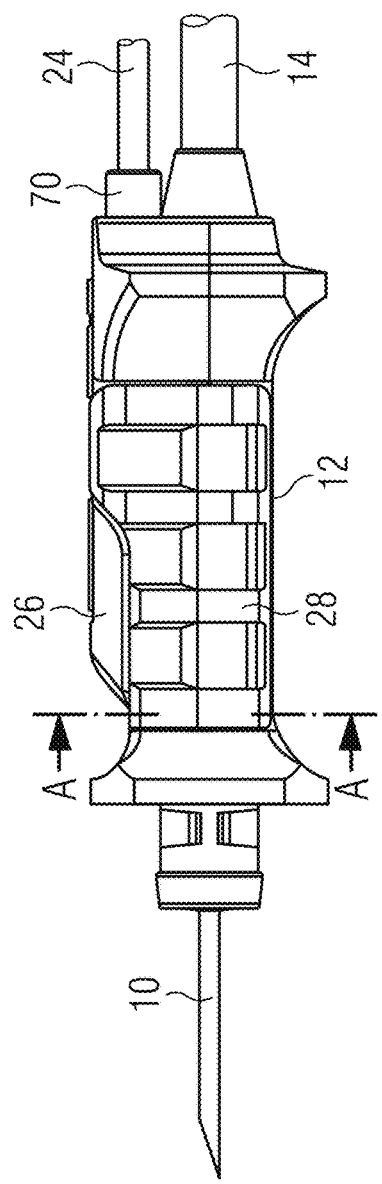
FIG. 27 shows a side view of a sixth embodiment of the unipolar cannula, with stimulation cable attached.
Figure 28:
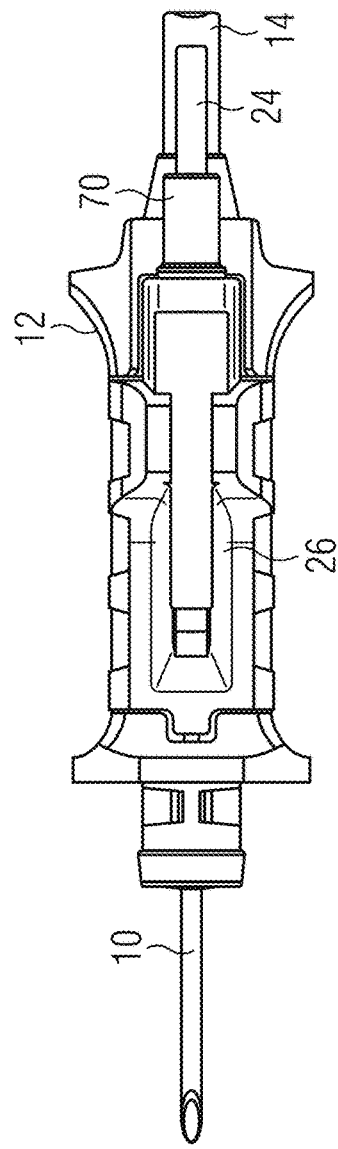
FIG. 28 shows a plan view of the sixth embodiment.
Figure 30:
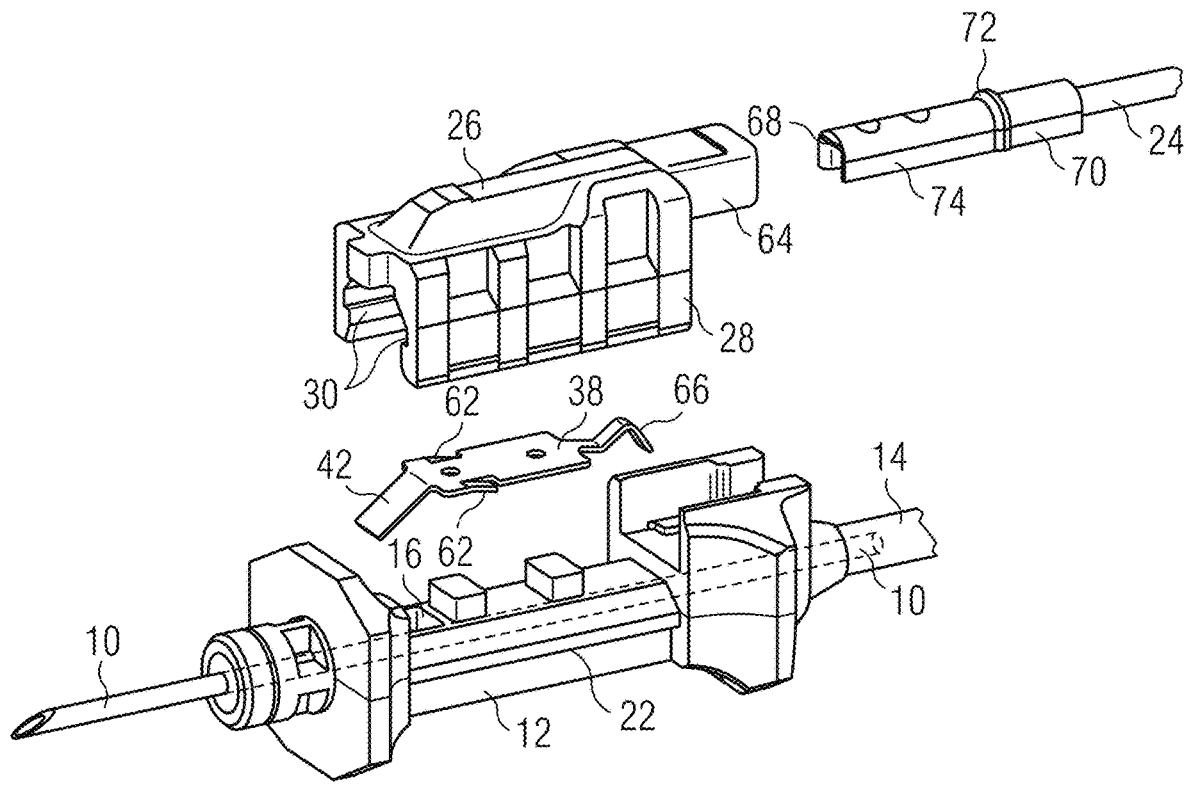
FIG. 30 shows an exploded view of the unipolar cannula with stimulation cable according to the sixth embodiment.
Figure 31:
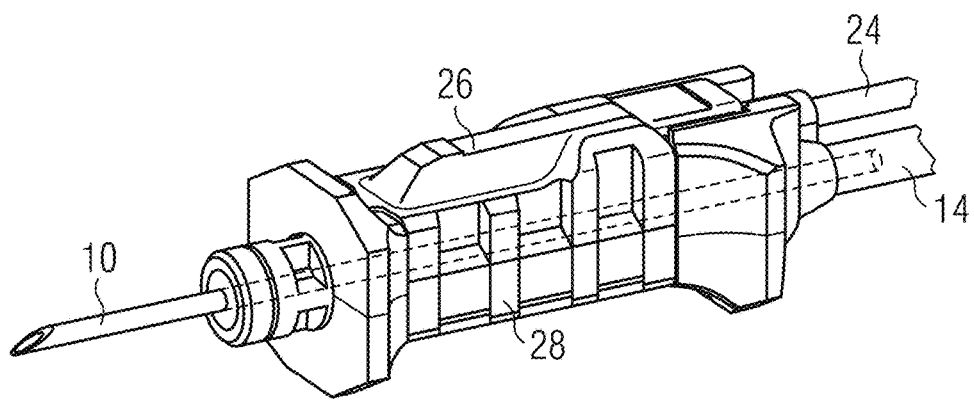
FIG. 31 shows a perspective view of the unipolar cannula of the sixth embodiment, with stimulation cable attached.
Figure 32:
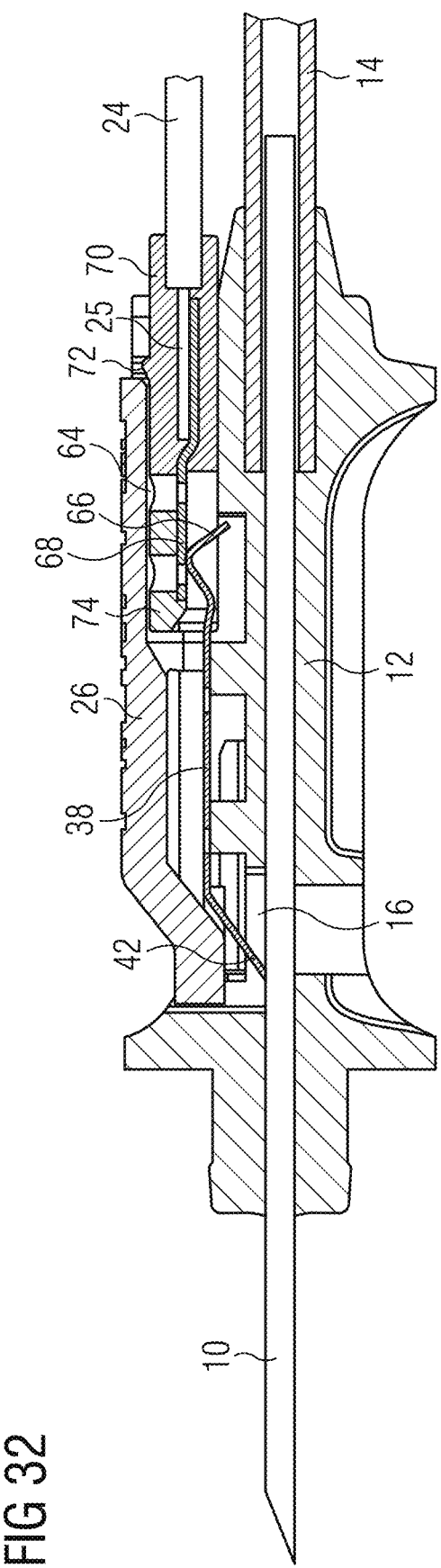
FIG. 32 shows an axial section of the unipolar cannula with stimulation cable attached, according to the sixth embodiment.

In this fifth embodiment, in place of the bearing pin and the bearing socket, a bearing nib 58 is molded onto the distal end of mounting part 26, which engages into recess 16. When the distal end of mounting part 26 is inserted into recess 16, bearing nib 58 engages into an opening 60 which is formed in the proximally-facing end face of forward flange 18. Mounting part 26 is thereby mounted at its distal forward end pivotably in flange 18 of body part 12 and can be pivoted from the position shown in FIG. 22 and FIG. 26b into the position shown in FIGS. 25 and 26c, respectively. When mounting part 26 comes to rest on body part 12 as a result of this pivoting movement, nib 30 of snap-locking arm 50 engages in a locking connection with inner step 22 in depression 52, as described in connection with the fourth embodiment. The snap connection is thereby produced and mounting part 26 is secured along with stimulation cable 24 on body part 12 and thus on the cannula.

In this embodiment as well, contact element 38 may be embodied as a spring tab 42 or as an insulation displacement contact 40.

FIGS. 27-32 show a sixth embodiment of the unipolar cannula. To the extent that this sixth embodiment is identical to the above-described embodiments, the same reference signs are used, and the foregoing description applies to this sixth embodiment as well. Whereas in the foregoing embodiments, wire 25 of stimulation cable 24 is permanently electroconductively connected to contact element 38, e.g. by soldering, welding or the like, in the sixth embodiment, stimulation cable 24 with its conductive wire 25 can be electroconductively connected to contact element 38 via a plug-in connection. In all other aspects, the sixth embodiment corresponds to the third embodiment shown in FIGS. 12-17.

Mounting part 26, which is made of plastic, is snapped laterally onto body part 12 of cannula tube 10 and fits into the peripheral contour of body part 12 on the outer surface thereof. Mounting part 26 has four pairs of snap-locking arms 28, spaced apart axially on mounting part 26. Snap-locking arms 28 engage around body part 12 and snap resiliently with inwardly directed nibs 30 behind inner steps 22 formed on both sides of body part 12 to attach mounting part 26 to body part 12.

Mounting part 26 receives contact element 38, which is embodied as a leaf spring and engages with a forward end embodied as spring tab 42 into recess 16 to electroconductively contact cannula tube 10. Of course, an insulation displacement contact, rather than a spring tab 42, may be formed on contact element 38 in this case as well. During assembly, contact element 38 is inserted into lateral guide grooves on the inside of mounting part 26 and is clamped and secured in these guide grooves by means of splayed spring tabs 62.

In the sixth embodiment, stimulation cable 24 can be conductively connected to contact element 38 by a plug-in connection, and thus separably, in order to contact cannula tube 10 via said contact element 38, which is attached to body part 12 by means of mounting part 26. For this purpose, the rear region of mounting part 26 comprises an axially parallel tunnel 64 which is open in the proximal direction and which is formed on one side by a U-shaped protrusion of mounting part 26 that is closed toward the outer periphery, and on the other side by the wall of body part 12. A spring arm 66 formed at the proximal end of contact element 38 protrudes into this tunnel 64. Spring arm 66 includes an upward bulge, so that its bulge protrudes into the open cross-section of tunnel 64.

A metal contact strip 68 is electroconductively attached, e.g. by soldering, welding or the like, to the unattached end of wire 25 of stimulation cable 24. A plastic sheath 70 is molded around the unattached ends of wire 25 and contact strip 68. The cross-section of plastic sheath 70 corresponds to the inner cross-section of tunnel 64, so that plastic sheath 70 can be inserted fittingly into the tunnel 64, where an outer bead 72 on the plastic sheath engages in an inner groove of the U-shaped profile of tunnel 64. The rear portion of plastic sheath 70 encompasses the unattached end of wire 25 and contact strip 68 and also encloses the insulation of stimulation cable 24. At the proximal forward end, plastic sheath 70 forms a U-shaped profile 74 which is open toward body part 12, with contact strip 68 extending at the base of U-shaped profile 74. When stimulation cable 24 is separated from the unipolar cannula and the body part 12 thereof, as illustrated in the exploded view of FIG. 30, U-shaped profile 74 protects the unattached, exposed end of contact strip 68 against inadvertent contact by the user. This reliably prevents injury to the user or damage to his/her glove caused by the metal contact strip 68. When stimulation cable 24 is inserted with plastic sheath 70 into tunnel 64 of mounting part 26, stimulation cable 24 extends axially parallel to the tube 14 of cannula tube 10. The U-shaped profile 74 of plastic sheath 70 protrudes far enough into tunnel 64 of mounting part 26 that the angled spring arm 66 of contact element 38 can engage from below into the U-shaped profile 74 and reliably contacts the contact strip 68 under the elastic spring pressure of its angled portion. The electroconductive connection of the wire 25 of stimulation cable 24 to cannula tube 10 via contact strip 68 and contact element 38 is thereby established.

The sixth embodiment has the advantage that mounting part 26 together with contact element 38 can remain mounted on body part 12 even when stimulation cable 24 is not needed and is not attached. As a result, body part 12 and mounting part 26 together have the same shape for the user, regardless of whether or not stimulation cable 24 is attached. As with all the other embodiments, mounting part 26 mounted on body part 12 covers contact element 38 on its outer periphery, insulating it fully.

LIST OF REFERENCE SIGNS 10 cannula tube
12 body part
14 tube
16 recess
18 forward flange
20 groove
22 inner step
24 stimulation cable
25 wire
26 mounting part
28 snap-locking arms
30 nibs
32 Longitudinal member
34 groove
36 rear flange
37 notch
38 contact element 40 insulation displacement contact
42 spring tab
44 grooves
46 bearing pin
48 bearing socket
50 snap-locking arm
52 depression
54 protrusion
56 depression
58 bearing nib
60 opening
62 spring tabs
64 tunnel
66 spring arm
68 contact strip
70 plastic sheath
72 outer bead
74 U-shaped profile

The invention claimed is:

1. A unipolar cannula comprising:
a metal cannula tube,
a body part made of an electrically insulating plastic and attached to a proximal end of the cannula tube,
a connector disposed on the body part for introduction of a liquid into the cannula tube,
a stimulation cable with an electroconductive wire that electrically contacts the cannula tube in a region of the body part,
a mounting part made of an electrically insulating plastic arranged to be removably mounted on the body part and resting laterally on an outer peripheral surface of the body part,
wherein the mounting part receives an electroconductive contact element, which electrically contacts the electroconductive wire, in such a way that on one side, the contact element engages into a recess of the body part and contacts the cannula tube, and on another side is outwardly covered and fully insulated by the mounting part when the mounting part is mounted on the body part,
wherein the mounting part is arranged to be mounted on the body part by an elastically resilient snap connection, and
wherein the mounting part engages around the body part with at least one pair of resilient snap-locking arms.

2. The unipolar cannula according to claim 1, wherein the contact element is disposed between the snap-locking arms and the snap-locking arms engage over the body part on both sides of the recess.

3. The unipolar cannula according to claim 1, wherein the contact element has an insulation displacement contact which is pressed onto the cannula tube.

4. The unipolar cannula according to claim 1, wherein the connector for introduction of the liquid is attached coaxially to the body part.

5. The unipolar cannula according to claim 4, wherein the connector is formed by a tube attached to the body part.

* * * * *